United States Patent [19]
Hulka

[11] Patent Number: 6,010,516
[45] Date of Patent: Jan. 4, 2000

[54] BIPOLAR COAPTATION CLAMPS

[76] Inventor: Jaroslav F. Hulka, 2317 Honeysuckle Rd., Chapel Hill, N.C. 27514

[21] Appl. No.: 09/045,404

[22] Filed: Mar. 20, 1998

[51] Int. Cl.⁷ .................................................. A61B 17/04
[52] U.S. Cl. .............................. 606/148; 606/51; 606/150
[58] Field of Search ........................... 606/45–52, 37–40, 606/205–210, 137–139, 120

[56] References Cited

U.S. PATENT DOCUMENTS

| | | | |
|---|---|---|---|
| H1745 | 8/1998 | Paraschac | 606/51 |
| 5,540,684 | 7/1996 | Hassler, Jr. | 606/51 |
| 5,603,711 | 2/1997 | Parins et al. | 606/51 |
| 5,827,281 | 10/1998 | Levin | 606/50 |

*Primary Examiner*—Michael Buiz
*Assistant Examiner*—Lien Ngo
*Attorney, Agent, or Firm*—Lathrop & Gage LC

[57] ABSTRACT

A bipolar electrosurgical instrument has first and second clamp members, each comprising an electrically conductive clamping surface, a clamp support and an intermediate electrically insulative spacing layer for joining the clamping surface to the blade support. The first and second clamp members are pivotally joined such that the respective clamping surfaces of each of the first and second clamp members are in facing relation and define a space between the first and second clamp member for capturing tissue. The instrument regulates the space between the first and second clamp member such that only a certain amount of tissue may be captured. The instrument further includes a mechanism for applying a voltage between the metal clamp supports of the first and second clamp members to coaptate the captured tissue.

18 Claims, 2 Drawing Sheets

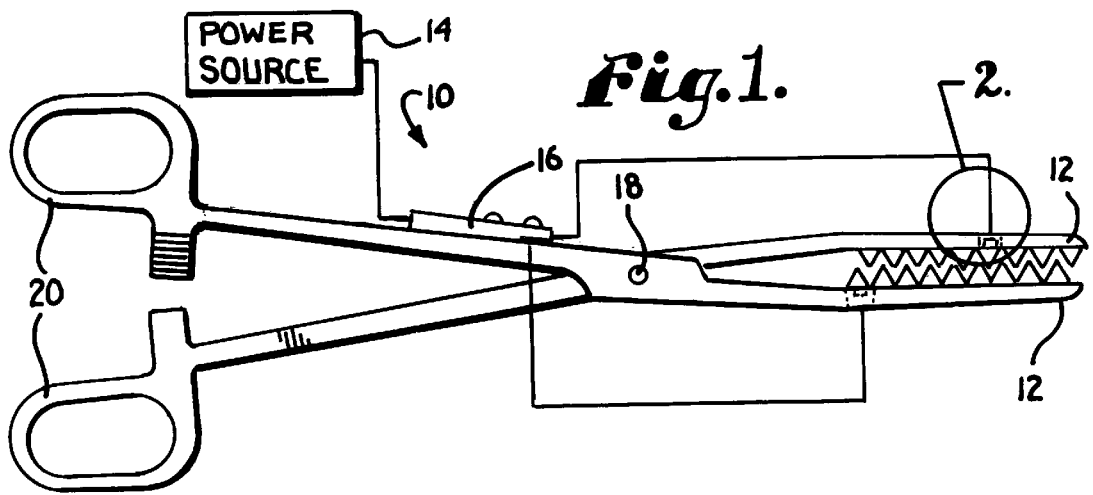
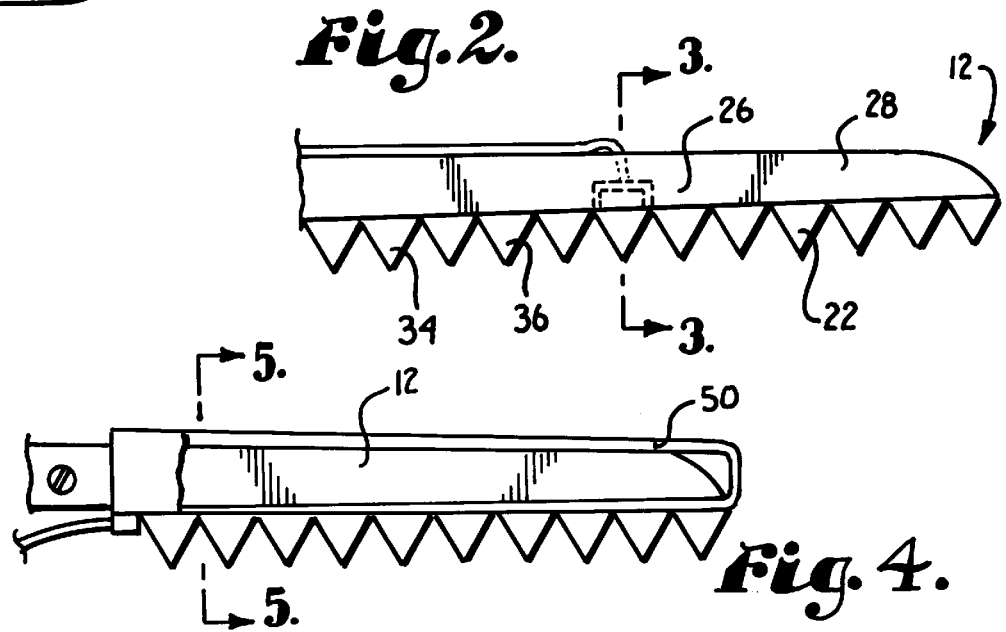
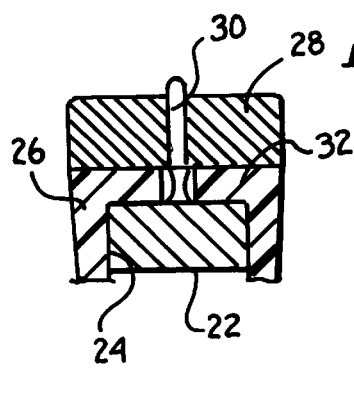
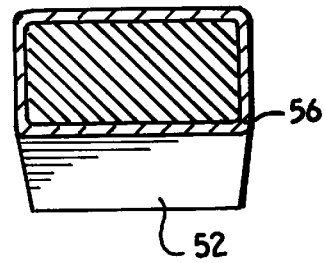

BIPOLAR COAPTATION CLAMPS

BACKGROUND OF THE INVENTION

1. Field of the Invention.

This invention relates generally to a bipolar electrosurgical instrument, and more particularly to an electrosurgical instrument that incorporates bipolar electrodes at each clamp member such that electrocoaptation can be achieved.

2. Discussion of Related Art.

In surgery, removal of diseased tissue results in bleeding by the healthy tissue. Traditionally, this bleeding has been controlled by clamping the tissue to mechanically squeeze the bleeding tissue, cutting the affected area and ligating the clamped pedicle.

Recently, electrocoagulating instruments have been used to accomplish this same objective. These instruments include at least one conductive electrode through which radio frequency energy is conducted to either a remote conductive body-plate (monopolar) or to a second, closely spaced conductive electrode (bipolar). Current passing through the gap between the two electrodes coagulates blood and other body fluids placed therebetween.

Monopolar electrocautery instruments suffer from the fact that the return path between the active electrode and the large-area body-plate can be unpredictable as the electrical current seeks the return electrode through the path of least resistance. In bipolar electrosurgical instruments, the two electrodes are closely spaced to one another, usually at the distal of an instrument handle. The return path is very short and only involves the tissue and fluids in the space between the electrodes.

A problem encountered with both monopolar and bipolar electrocoagulation instruments is the failure to control completely the bleeding due to larger vessels. While the use of electricity for hemostasis is appropriate for capillaries and smaller vessels that are sealed by coagulation of the blood in the vessels, larger arteries and vessels need to be sealed by coaptation-the compression and fusion of the inner walls of the occluded artery.

For example, bipolar scissors have been developed with blades at the distal tip performing coagulation and cutting of the tissue with a mechanical shearing action. The two blades are insulated from one another, allowing them to function as bipolar electrodes for electrocoagulating small blood vessels in the surgical field. U.S. Pat. No. 5,352,222 discloses such a surgical scissor with bipolar features. While these instruments are utilized for coagulation of smaller vessels, it is impossible to approximate larger arteries and veins to achieve coaptation. A need thus exists for an instrument to crush larger arteries and veins to approximate and coaptate these tissues using RF energy.

Another concern with electrosurgical instruments is the lateral spread of current to adjacent tissue. Unregulated current flow damages this adjacent tissue, which is not intended to be coagulated or cauterized. Present-day, bi-polar electrosurgical forceps and clamps used in endoscopy do not exert sufficient force to crush tissues such as ligaments sufficiently to consistently compress and coaptate the arteries and veins therein. Thus, because the distance between these instruments' clamp surfaces and therefore the volume of the crushed tissue is determined by the thickness of the dense tissue captured therein, the current flow at the edge of the electrode arcs outwardly into the surrounding normal tissue at uneven and unpredictable rates. Thus a need exists for an instrument that distributes crushing force and creates a consistent final volume of the tissue captured between the clamping surfaces of the clamp.

A need therefore exists for a bipolar electrosurgical clamp to perform compression and controlled bipolar electrocoagulation and electrocoaptation of large arteries and veins.

SUMMARY OF THE INVENTION.

It is accordingly a principal object of the present invention to provide a bipolar, electrocoaptation clamp.

The foregoing object of the invention is achieved by providing a bipolar electrosurgical instrument having first and second clamp members, each comprising a metal clamping surface defining a periphery, a clamp support, and an insulative coating surrounding the periphery of each metal clamping surface. The first and second clamp members are pivotally joined such that the respective clamping surfaces of each of the first and second clamp members are in facing relation and movable between a tissue-accepting position wherein the respective clamping surfaces of the first and second clamp member are spaced apart and a closed position wherein the tissue is crushed therein between. The instrument further includes a mechanism for applying a voltage between the metal clamp surfaces of the first and second clamp members to coaptate the captured tissue and a mechanism to regulate the voltage applied to the metal clamping surfaces.

In an alternative embodiment, the foregoing object of the invention is achieved by providing a bipolar electrosurgical clamp for coaptation of tissue comprising first and second clamp members. Electrically conductive sheaths are removably mounted on the first and second clamp members. The first and second clamp members are pivotally joined such that the tissue grasping surfaces of the sheaths are in facing relation and movable between a tissue-accepting position having a space between the surfaces and a closed position wherein the tissue is crushed therein between. The instrument further includes a mechanism for applying a voltage between the sheaths as mounted on the first and second clamp members as said first and second clamp members are in said closed position, and for regulating the voltage to achieve coaptation of the tissue.

The foregoing features, objects and advantages of the invention will become apparent to those skilled in the art the following detailed description of a preferred embodiment.

DESCRIPTION OF THE DRAWINGS

FIG. 1 is a side elevation view of a bipolar electrosurgical clamp constructed in accordance with the present invention;

FIG. 2 is an elevation view of one of the clamp members associated with the electrosurgical clamp of the present invention;

FIG. 3 is a cross section taken along lines 3—3 of FIG. 2;

FIG. 4 is an elevation view of one of the clamp members associated with an alternative embodiment of the electrosurgical clamp of the present invention;

FIG. 5 is a cross section taken along lines 5—5 of FIG. 4; and

DESCRIPTION OF THE PREFERRED EMBODIMENT

Figure 6:
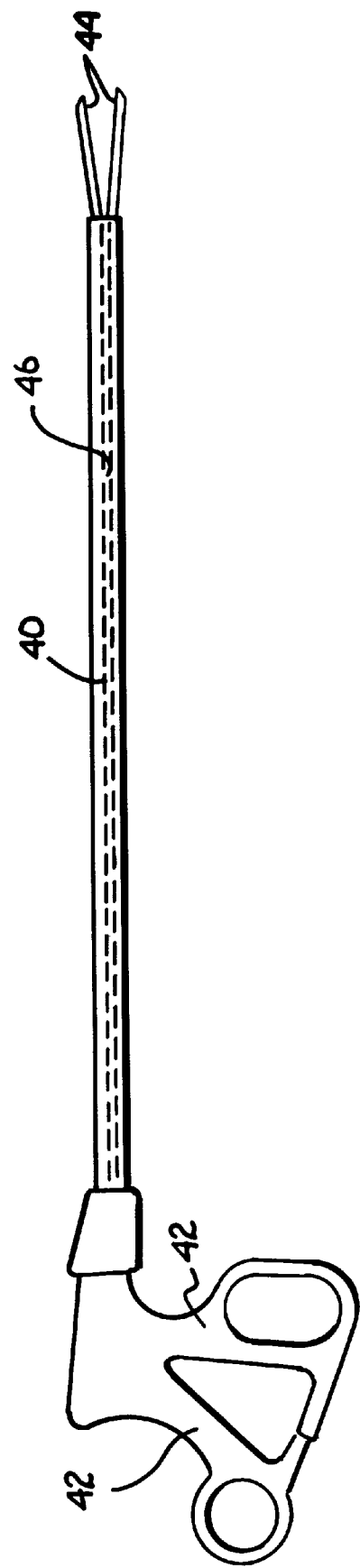
FIG. 6 is an elevation view of a second alternative embodiment of the electrosurgical clamp of the present invention.

Referring to FIG. 1, a bipolar electrosurgical instrument of the present invention is indicated generally at 10. The electrosurgical instrument 10 includes first and second clamp members, each indicated generally at 12, a current-source 14 for applying and regulating a voltage between the clamp members, and a mechanism 16 for indicating when coaptation of the tissue is achieved.

The first and second clamp members, 12 are pivotally joined to each other by an insulated rivet or screw 18, which extends through aligned bores (not shown) formed through each clamp member. As such, both clamp members 12 are pivotally moveable with respect to each other. The clamp 10 includes a standard clamp handle 20 at its proximal end for open surgery, as depicted in FIG. 1. At its distal end, each clamp member 12 includes a metal clamping surface 22, which defines a periphery 24, an insulative coating 26 surrounding the periphery of each metal clamping surface, and a clamping support 28, as shown in FIGS. 2 and 3. The support 28 is fabricated of a sufficient thickness to withstand the stresses encountered in compressing and crushing tissue. Preferably, the support 28 is approximately at least 4 mm. in thickness.

The first and second clamp members 12 are pivotally joined such that the clamping surfaces 22 of said first and second clamp members are in facing, substantially parallel relation and movable between a tissue-accepting position having a space between the opposed clamping surfaces and a closed position wherein the tissue is crushed therein between. The clamping surfaces 22 remain substantially parallel from the tissue-accepting position to the closed, crushing position, which allows for consistent application of crushing force on the tissue.

At least a portion of the facing surface of each support is the clamping surface 22 and this portion 22 is formed of an electrically conductive material. As such, the clamping surface 22 of each clamping member 12 acts as an electrode and is made of metal, preferably stainless steel. As shown in FIG. 2, the support is formed with an aperture 30 to permit the electrode to be wired to a remote source of electrical energy 14.

The clamping surface 22 defines a periphery 24. Surrounding this periphery 24 is an electrically insulative coating 26, which extends upwardly along the side of the distal end of the clamp member 12. This coating 26 insures that as captured tissue is being coaptated, the current flowing between the respective clamp members 12 is controlled such that the current flow laterally away from the clamping surface through surrounding tissue is minimized. Preferably, an additional intermediate electrically insulative layer 32 is disposed between the clamp surface 22 and the support 28 for each clamp member. These layers 32 act to bond each clamping 22 surface to its respective support. The insulative coating 26 and intermediate layer 32 can be made of any suitable insulating material and preferably a non-conductive adhesive such as an epoxy adhesive. In an alternative embodiment, the entire support may be constructed of an insulative material such as TEFLON™.

The grasping surface 34 of each clamp member is a generally elongate and preferably, the grasping surface is approximately 4 mm. in width and 20 mm. in length. An array of teeth 36 extend laterally across each jaw assembly, as exemplified in FIG. 2. The first clamp member's array of teeth is displaced by one-half pitch from the teeth of the second grasping member's grasping surface's set of teeth. This arrangement of teeth allows the grasping members to mate and effectuates proper alignment as the clamping members 12 are pivoted to the closed position to engage and crush tissue between the opposed clamping surfaces 22.

The compressive force applied to the tissue by the clamp 10 of the present invention will be sufficient to crush the tissue to a consistent minimum volume between the substantially parallel clamping surfaces of the first and second members 12. This minimizes and makes consistent the distance between the electrodes 22 for the electric current to flow between, and, in conjunction with the electrically insulative material surrounding the periphery 24 of the electrode, minimizes lateral spread of normal tissue coagulation by minimizing the lateral arcing of current flow at the edge of the electrodes.

Another aspect of this compressive force applied to the clamps 10 is that blood vessel walls within the crushed tissue will be approximated and crushed together to accomplish coaptation. Coaptation will be ensured by electrocoagulation prior to removal of the clamp, allowing division of the crushed and coagulated tissue without bleeding.

A generator 14 provides electrosurgical energy to each clamp members 12 grasping surface 34 and is activated by the user. The generator 14 is an electrosurgical unit capable of providing bipolar energy. The energy is delivered through electrically insulated wires that extend along the length of the instrument to the electrodes. In a preferred embodiment, the wires extend through bores within each clamping member 12 from a proximal end of each member 12 to the distal end.

A current indicator 16 is shown located on the instrument handle and includes a LED display, which indicates whether coagulation and coaptation process is complete. A sensor (not shown) is incorporated in the power source 14. As the sensor indicates a steady-state tissue impedance level, the indicator 16 will generate a signal to the user that coaptation is complete.

As electric current passes through tissue, it heats the tissue and causes all water and most fluid to evaporate (desiccation). The evaporated tissue acts as an electrical insulator with high electrical resistance. The low steady-state current flow signal detected by the sensor indicates that the coagulation of the blood and vessel wall necessary for coaptation has been completed and the coaptation process is complete. This end-point will be indicated by the LED indicator 16 on the handle of the clamp 10 so the surgeon will know that the clamp may be removed.

For endoscopic applications, the bipolar electrosurgical instrument includes an elongate tubular body 40 of a diameter (5to 10 mm) and length (at least 32 cm) sufficient for use in endoscopy using a scope-type instrument, as shown in FIG. 6. The tubular body 40 has a proximal end affixed to a handle assembly 42, a distal end securing the first and second clamp members 44, and a lumen 46 that extends for the entire length of the tubular body 40. The tubular body 40 comprises a metal tube, constructed of stainless steel or other suitable material, and coated over its exterior with an electrical insulator. Alternatively, the tubular body 40 may be constructed of an electrically insulative material such as TEFLON. The coaptation clamp is removably connected to the distal end of the tubular member. As such, after use the clamp may be removed and disposed.

Two conductive wires extend from an electrical source 14 through the tubular member from the electrical connector (not shown) located on the handle assembly to the conductive clamping surface. The conductive wire has an insulative covering to keep the wires electrically isolated and prevent any short circuiting. In this embodiment, it is preferable to use a triple lumen tube that extends through the tubular member. The rod and conductive wires can extend through their individual lumens electrically isolated from each other and further to support them along their length.

The mechanism for opening and closing the grasping members of the instrument comprises a single, non-conductive push rod and corresponding linkage. It will be understood that any actuation mechanism that results in dual or single pivotal movement of the grasping members may be used without departing from the scope of the present invention.

In an alternative embodiment shown in FIGS. 4 and 5, the bipolar electrosurgical clamp 10 for coaptation of tissue has first and second clamp members 12, and electrically conductive sheaths 50, which are removably mountable on the first and second clamp members. Each sheath 50 comprises an electrically conductive clamping portion 52, which defines a periphery 54, and an insulative coating 56 surrounding the periphery. The first and second clamp members 12 are pivotally joined such that the clamping portion of the sheaths are in facing relation and movable between a tissue-accepting position having a space between the surfaces and a closed position wherein the tissue is crushed therein between.

The electrically insulative coating 56 surrounds the periphery 54 and preferably extends along the remainder of the sheath and thus extends around each clamp member 12. This coating insures that as captured tissue is being coaptated, the current flowing between the respective clamp members is controlled such that current flowing laterally away from the clamping surface through surrounding tissue is minimized. The insulating coating can be made of any suitable insulating material, such as TEFLON.

The instrument further includes a generator 14 for applying a voltage between the sheaths 50 as mounted on the first and second clamp members in the closed position, and for regulating the voltage to achieve coaptation of the tissue. The generator 14 provides electrosurgical energy to the clamping portion of each sheath and is activated by the user. The generator 14 uses an electrosurgical unit capable of providing bipolar energy. The energy is delivered through electrically insulated wires that extend from the distal handles along the length of the instrument and to the electrodes, i.e., the electrically conductive clamping portion of each sheath. Preferably, the wires extend through bores within each clamping member and are releasably connected to the sheaths. Preferably, the sheaths are formed with male connectors that are releasably mateable with female connectors formed in the clamp.

A current indicator 16 is shown located on the instrument handle (FIG. 1) and includes a LED display, which indicates whether coaptation is complete. A sensor (not shown) is in the generator. As the sensor indicates a steady-state tissue impedance level, the indicator will generate a signal to the user that coaptation is complete.

In use, the bipolar electrocoagulating instrument 10 captures the selected tissue in the tissue-accepting gap. The clamp members are pivoted to grasp and crush the tissue in between the members 12. This minimizes and makes consistent the distance between the electrodes 22 for the electric current to flow between. Further, this compressive force applied to the clamp members 12 ensures that blood vessel walls within the crushed tissue will be approximated and crushed together.

A regulated RF current is applied to the electrically conductive grasping surfaces and the tissue captured between the clamping surfaces is coagulated and coaptated. The sensor of the power source will detect a steady-state impedance level upon coaptation, which will activate the LED indicator 16. The surgeon then removes the clamp from the coaptated tissue.

Coaptation occurs by electrocoagulation prior to removal of the clamp, allowing division of the crushed and coagulated tissue without bleeding. In conjunction with the electrically insulative material surrounding the periphery 24 of the electrode, electro-coagulation through the instrument described herein minimizes lateral spread of normal tissue coagulation by minimizing the lateral arcing of current flow at the edge of the electrodes.

There has been described several embodiments of a bipolar electrosurgical instrument. While these particular embodiments have been described in detail, it is not intended that the invention be limited thereto, as it is intended that the invention be as broad in scope as the art will allow and the specification be read likewise. It will therefore be appreciated by those skilled in the art that yet other modifications could be made to the provided invention without departing from the scope as so claimed by the present invention.

What is claimed is:

1. A bipolar electrosurgical instrument for coaptation of tissue, comprising
    first and second clamp members each comprising a metal clamping surface defining a periphery, a clamp support, and an insulative coating surrounding the periphery of each metal clamping surface;
    a connector pivotally connecting the first and second clamp members such that the clamping surfaces of the first and second clamp members are in facing relation;
    a power source configured to apply a voltage between the metal clamp supports of the first and second clamp members; and
    a regulator configured to regulate the voltage to achieve coaptation of the tissue;
    wherein the first and second clamp members are configured to crush tissue between the clamping surfaces when the clamping surfaces are moved between a tissue-accepting position and a closed position.

2. The bipolar electrosurgical instrument of claim 1, wherein each clamp member further comprises an intermediate electrically insulative spacing layer disposed between the clamping surface and clamp support.

3. The bipolar electrosurgical instrument of claim 1, wherein each clamp member is made of an electrically conductive material, and wherein the connector comprises an electrically insulating hinge separating the first and second clamp members.

4. The bipolar electrosurgical instrument of claim 1, wherein the clamping surface of each clamp member comprises an array of teeth.

5. The bipolar electrosurgical instrument of claim 1 wherein the relulator comprises a sensor operatively coupled to the power source and configured to measure a current flow through the tissue and an indicator to display a change in current flow that corresponds to the coaptation of the tissue.

6. The bipolar electrosurgical instrument of claim 1 wherein the power source further is configured to control an amount of current to assure a regulated coaptation.

7. The bipolar electrosurgical instrument of claim 6 wherein the power source is configured to output approximately between 20–25 Watts of power.

8. The bipolar electrosurgical instrument of claim 7 wherein the power source applies the current for approximately 15 to 20 seconds.

9. The bipolar electrosurgical instrument of claim 1, wherein the clamping surface of each clamp member has a width of approximately 4 mm.

10. A bipolar electrosurgical clamp for coaptation of tissue, comprising first and second clamp members;

electrically conductive sheaths removably mounted on the first and second clamp members, each sheath having a tissue-grasping surface;

a connector pivotally connecting the first and second clamp members such that the tissue-grasping surfaces of the first and second clamp members are in facing relation;

a power source configured to apply a voltage between the sheaths as mounted on the first and second clamp members; and a regulator configured to regulate the voltage to achieve coaptation of the tissue;

wherein the first and second clamp members are configured to crush tissue between the tissue-grasping surfaces when the tissue-grasping surfaces are moved between a tissue-accepting position and a closed position.

11. The bipolar electrosurgical instrument of claim 10, wherein each sheath comprises an electrically conductive clamping portion defining a periphery and an insulative coating surrounding the periphery.

12. The bipolar electrosurgical instrument of claim 11 wherein the regulator comprises a sensor operatively coupled to the power source and adapted to measure a current flow through the tissue and an indicator to display a change in current flow that corresponds to the coaptation of the tissue.

13. The bipolar electrosurgical instrument of claim 12 wherein the power source further is configured to control an amount of current to assure a regulated coaptation.

14. The bipolar electrosurgical instrument of claim 13 wherein the power source is configured to output approximately between 20–25 Watts of power.

15. The bipolar electrosurgical instrument of claim 14 wherein the power source is configured to output the current for approximately 15 to 20 seconds.

16. The bipolar electrosurgical instrument of claim 11 wherein each sheath further comprises an array of teeth.

17. The bipolar electrosurgical instrument of claim 11 wherein each sheath is disposable.

18. A bipolar electrosurgical instrument for coaptating tissue, the instrument comprising first and second clamp members each comprising a proximal end and a distal end, the proximal end of each clamp member having a finger-receiving portion to receive the fingers of a user, the distal end of each clamp member having a metal clamping surface defining a periphery, a clamp support, and an insulative coating surrounding the periphery;

a connector pivotally connecting the first and second clamp members such that the clamping surfaces of the first and second clamp members are in facing relation;

an electrical source for applying a voltage between the clamping surfaces of the first and second clamp members;

a sensor configured to measure a current flow between the clamping surfaces of the first and second clamping members; and a coaptation indicator configured to signal that the tissue captured between the clamping surfaces of the clamping members is coaptated;

wherein the first and second clamp members are configured to crush tissue between the clamping surfaces when the clamping surfaces are moved between a tissue-accepting position and a closed position.

* * * * *